United States Patent
Mautner et al.

(10) Patent No.: US 8,367,856 B2
(45) Date of Patent: Feb. 5, 2013

(54) METHOD FOR PREPARING ALKYL CHLOROSILANES THROUGH REARRANGEMENT REACTIONS

(75) Inventors: Konrad Mautner, Riesa (DE); Werner Geissler, Thiendorf (DE); Gudrun Tamme, Moritzburg (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/119,355

(22) PCT Filed: Oct. 26, 2009

(86) PCT No.: PCT/EP2009/064092
§ 371 (c)(1),
(2), (4) Date: Mar. 16, 2011

(87) PCT Pub. No.: WO2010/049395
PCT Pub. Date: May 6, 2010

(65) Prior Publication Data
US 2011/0196165 A1    Aug. 11, 2011

(30) Foreign Application Priority Data
Oct. 30, 2008   (DE) .......................... 10 2008 043 331

(51) Int. Cl.
*C07F 7/14* (2006.01)
(52) U.S. Cl. ..................................................... 556/469
(58) Field of Classification Search .............. 556/469, 556/478, 466, 472; 423/342
See application file for complete search history.

(56) References Cited

U.S. PATENT DOCUMENTS

| | | | |
|---|---|---|---|
| 3,793,357 A | | 2/1974 | McEntee |
| 6,175,029 B1 * | | 1/2001 | Colin ............................ 556/469 |
| 2003/0109735 A1 * | | 6/2003 | Tsukuno et al. .............. 556/469 |

FOREIGN PATENT DOCUMENTS

EP   0 146 148   6/1985

OTHER PUBLICATIONS

International Search Report for PCT/EP2009/064092 dated Jan. 18, 2010.

* cited by examiner

*Primary Examiner* — Johann Richter
*Assistant Examiner* — Pancham Bakshi
(74) *Attorney, Agent, or Firm* — Caesar, Rivise, Bernstein, Cohen & Pokotilow, Ltd.

(57) ABSTRACT

The object of the invention is a method for preparing silanes of the general formula (1) $R_aH_bSiCl_{4-a-b}$ (1), wherein mixtures of silanes of the general formulas (2) and (3) $R_cSiCl_{4-c}$ (2), $R_dH_eSiCl_{4-d-e}$, where R indicates an alkyl radical with 1 to 6 carbon atoms, a indicates the values 1, 2 or 3, b indicates the values 0 or 1, c indicates the values 1, 2, 3 or 4, d indicates the values 0, 1 or 2 and e indicates the values 0, 1 or 2, are reacted in the presence of an aluminum oxide catalyst comprising 1 to 10 parts by weight of aluminum chloride and 0.5 to 10 parts by weight of a metal oxide selected from magnesium oxide, copper oxide, zinc oxide and mixtures thereof to 100 parts by weight of aluminum oxide.

7 Claims, No Drawings

METHOD FOR PREPARING ALKYL CHLOROSILANES THROUGH REARRANGEMENT REACTIONS

BACKGROUND OF THE INVENTION

The invention relates to a process for preparing alkyl chlorosilanes which may have hydrogen in the presence of an alumina catalyst.

The preparation of alkylchlorosilanes by direct synthesis (Müller-Rochow synthesis) results, apart from the main dialkyldichlorosilane product, in further silanes such as tetraalkylsilane, trialkylchlorosilane, alkyltrichlorosilane inter alia, for which there is a varying demand and, in the event of an excess, a possible use is required. In the distillation of the crude silane mixture from the direct synthesis of alkylchlorosilanes and chlorosilanes, first runnings and intermediate fractions are also obtained, which cannot be utilized directly for further processing.

For instance, it is well known from the literature that aluminum chloride in all forms catalyzes the rearrangements, even on support materials such as aluminas. In US20030109735, the conversion in the trimethylsilane+methyltrichlorosilane or trimethylchlorosilane+methyltrichlorosilane reactions is improved by adding, for example, magnesium oxide to the aluminum chloride. DE 2351258 describes the addition of promoters to those reactions which minimize the discharge of aluminum chloride from the reaction vessel. EP 0971932, in contrast, describes the use of very pure alumina as a catalyst. The use of zeolites has also been described adequately, such as in EP 0146148.

It is an object of the invention to perform all conceivable rearrangement reactions in an apparatus with a very effective catalyst, not just with the pure substances, but also with mixtures of silanes with chlorine, hydrogen and alkyl radicals as substituents.

SUMMARY OF THE INVENTION

The invention provides a process for preparing silanes of the general formula (1)

$$R_aH_bSiCl_{4-a-b} \quad (1)$$

in which mixtures of silanes of the general formulae (2) and (3)

$$R_cSiCl_{4-c} \quad (2)$$

$$R_dH_eSiCl_{4-d-e} \quad (3)$$

where
R is an alkyl radical having 1 to 6 carbon atoms,
a is 1, 2 or 3,
b is 0 or 1,
c is 1, 2, 3 or 4,
d is 0, 1 or 2 and
e is 0, 1 or 2,
are converted in the presence of an alumina catalyst which comprises, per 100 parts by weight of alumina, 1 to 10 parts by weight of aluminum chloride and 0.5 to parts by weight of a metal oxide selected from magnesium oxide, copper oxide, zinc oxide and mixtures thereof.

DETAILED DESCRIPTION OF PREFERRED EMBODIMENTS

The preparation of silanes of the general formula (1) is accelerated considerably by the proportions of aluminum chloride and metal oxide compared to the pure alumina. The reactions of silanes of the general formulae (2) and (3) are rearrangement reactions.

Preferably, the R radical has 1 to 3 carbon atoms. More particularly the R radical is a methyl or ethyl radical.

Preferred products are dialkyldichlorosilane, trialkylchlorosilane and alkylhydrochlorosilanes.

Preference is given to performing rearrangement reactions [1] to [11]:

$$CH_3SiCl_3 + H_2SiCl_2 \longrightarrow CH_3HSiCl_2 \quad [1]$$

$$(CH_3)_2SiCl_2 + H_2SiCl_2 \longrightarrow CH_3HSiCl_2 + (CH_3)_2HSiCl \quad [2]$$

$$(CH_3)_3SiCl + H_2SiCl_2 \longrightarrow CH_3HSiCl_2 + (CH_3)_2HSiCl \quad [3]$$

$$(CH_3)_3SiCl + (CH_3)SiCl_3 \longrightarrow (CH_3)_2SiCl_2 \quad [4]$$

$$(CH_3)_3SiCl + (CH_3)HSiCl_2 \longrightarrow (CH_3)_2HSiCl \quad [5]$$

$$(CH_3)_3SiCl + HSiCl_3 \longrightarrow (CH_3)_2SiCl_2 + CH_3HSiCl_2 + (CH_3)_2HSiCl \quad [6]$$

$$(CH_3)_3SiCl + SiCl_4 \longrightarrow CH_3SiCl_3 + (CH_3)_2SiCl_2 \quad [7]$$

$$CH_3SiCl_3 + (CH_3)_4Si \longrightarrow (CH_3)_2SiCl_2 + (CH_3)_3SiCl \quad [8]$$

$$(CH_3)_4Si + (CH_3)_2SiCl_2 \longrightarrow (CH_3)_3SiCl \quad [9]$$

$$(CH_3)_4Si + SiCl_4 \longrightarrow CH_3SiCl_3 + (CH_3)_2SiCl_2 + (CH_3)_3SiCl \quad [10]$$

$$(CH_3)_4Si + HSiCl_3 \longrightarrow (CH_3)_2SiCl_2 + (CH_3)_3SiCl + (CH_3)_2HSiCl \quad [11]$$

The alumina may be alpha- or preferably gamma-alumina.

The alumina catalyst preferably comprises 3 to 6 parts by weight of aluminum chloride per 100 parts by weight of alumina. The alumina catalyst preferably comprises 1 to 5 parts by weight of the metal oxide per 100 parts by weight of alumina. The metal oxides or mixed oxides used may be any desired oxides or mixed oxides of the metals magnesium, copper and zinc. Particular preference is given to magnesium oxide.

The alumina catalyst preferably has a BET surface area of at least 100 m²/g, more preferably at least 230 m²/g and preferably at most 600 m²/g. The alumina catalyst preferably has a pore volume of at least 0.2 cm³/g, more preferably at least 0.5 cm³/g and preferably at most 1.5 cm³/g.

The alumina catalyst used is preferably an alumina-metal oxide support material which has been coated with aluminum chloride.

The alumina catalyst can be used in the form of a powder or preferably in the form of a shaped body.

The process is performed preferably at at least 180° C., more preferably at least 200° C., especially at least 220° C., and preferably at most 370° C., more preferably at most 350° C., especially at most 300° C. The process is performed preferably at at least 1 bar, more preferably at least 2 bar, especially at least 4 bar, and preferably at most 30 bar, more preferably at most 15 bar, especially at most 10 bar.

Suitable reactors for the process are all temperature-controllable apparatuses which allow easy handling of the solid catalyst. Particular preference is given to using tubular reactors with heat carrier circulation, which allow a favorable temperature regime.

Since silane of the general formula (3) in which e has the value of 1 or 2 also promotes reactions between silanes of the general formulae (2) and (3) in which e in the general formula (3) has the value of 0, preference is given to adding silane of the formula (3) in which e has the value of 1 or 2 in such reactions. Silane of the general formula (3) in which e has the value of 1 or 2 therefore has cocatalytic action. The proportion of silane of the general formula (3) in which e has the value of 1 or 2 in the mixture of silanes of the general formulae (2) and (3) used is preferably at least 0.5% by weight, more preferably at least 5% by weight, especially at least 10% by weight.

The silanes of the general formula (3) in which e has the value of 1 or 2 used may also be used as mixtures, for example as a distillate fraction in which, for example, $CH_3HSiCl_2$, $(CH_3)_2HSiCl$ and $HSiCl_3$ are present.

The alumina catalyst is preferably prepared by treating alumina which comprises the metal oxides with hydrogen chloride at preferably at least 100° C., more preferably at least 180° C. and preferably at most 250° C.

Subsequently, the alumina catalyst thus produced is dried in a hot gas stream, preferably under reduced pressure, or with trimethylchlorosilane.

All above symbols in the above formulae are each defined independently of one another. In all formulae, the silicon atom is tetravalent.

In the examples and comparative examples which follow, unless stated otherwise in each case, all amount and percentage data are based on weight, and all reactions are performed at a pressure of 6.5 bar (abs.) and a temperature of 300° C.

For the silanes, the following abbreviations have been used in the tables:
TCS: trichlorosilane
M1: methyltrichlorosilane
M2: dimethyldichlorosilane
M3: trimethylchlorosilane
HM: methylhydrodichlorosilane
HM2: dimethylhydrochlorosilane The examples were carried out in a heat carrier-heated, continuously operated tubular reactor made from Hastelloy® HB3 with diameter 50 mm and length 700 mm, with an upstream reactant evaporator, a heat carrier feed temperature of 300° C. and a reactor pressure of 5.5 bar gauge. The reactor was filled with pretreated alumina extrudate of approx. 2.5*8 mm.

The pure alumina had a BET surface area of 247 m²/g and a pore volume of 0.9 cm³/g. The alumina with 2% added magnesium oxide had a BET surface area of 227 m²/g and a pore volume of 0.87 cm³/g. The treatment in a hydrogen chloride stream formed 4.5% aluminum chloride from the alumina.

The products were analyzed by means of GC (calibrated to % by mass).

EXAMPLE 1

The amount of catalyst is 1.5 l. The process according to the invention can increase the throughput at constant conversion.

| Alumina | Reactant throughput | Molar reactant ratio | Target products |
|---|---|---|---|
| pure * | 300 g/h | 1M1:1M3 + 5% HM | 36.8 % M2 |
| with 2% MgO | 500 g/h | 1M1:1M3 + 5% HM | 36 % M2 |

* noninventive

EXAMPLE 2

The amount of catalyst is 0.5 l. The process according to the invention can increase the yield at the same throughput.

| Alumina | Reactant throughput | Molar reactant ratio | Target products |
|---|---|---|---|
| pure * | 100 g/h | 1M1:1M3 + 5% HM | 32% M2 |
| with 2% MgO | 100 g/h | 1M1:1M3 + 5% HM | 51% M2 |

* noninventive

EXAMPLE 3

The amount of catalyst is 1.5 l. The process according to the invention can significantly increase the throughput.

| Alumina | Reactant throughput | Molar reactant ratio | Target products |
|---|---|---|---|
| pure * | 1000 g/h | 1M3:1HM | 13% HM2 |
| with 2% MgO | 1800 g/h | 1M3:1HM | 13% HM2 |

* noninventive

EXAMPLE 4

The amount of catalyst is 0.5 l. The process according to the invention can increase the yield at the same throughput.

| Alumina | Reactant throughput | Molar reactant ratio | Target products |
|---|---|---|---|
| pure * | 110 g/h | 1M3:2 TCS | 24% M2 + 0.4% HM2 + 3% HM |
| with 2% MgO | 110 g/h | 1M3:2 TCS | 41% M2 + 2% HM2 + 5% HM |

* noninventive

The invention claimed is:
1. A process for preparing silanes of the general formula (1),

$$R_aH_bSiCl_{4-a-b} \quad (1)$$

said process comprising converting mixtures of silanes of the general formulae (2) and (3)

$$R_cSiCl_{4-c} \quad (2)$$

$$R_dH_eSiCl_{4-d-e} \quad (3)$$

where
R is an alkyl radical having 1 to 6 carbon atoms,
a is 1, 2 or 3,
b is 0 or 1,
c is 1, 2, 3 or 4,
d is 0, 1 or 2 and
e is 0, 1 or 2,
in the presence of an alumina catalyst which comprises, per 100 parts by weight of alumina, 1 to 10 parts by weight of aluminum chloride and 0.5 to 10 parts by weight of a metal oxide selected from the group consisting of magnesium oxide, copper oxide, zinc oxide and mixtures thereof, wherein the temperature is 180 degree C. to 370 degree C.
2. The process as claimed in claim 1, wherein R is a methyl or ethyl radical.

3. The process as claimed in claim 1, wherein the alumina catalyst has a BET surface area of at least 100 m$^2$/g.

4. The process as claimed in claim 1, wherein the alumina catalyst has a pore volume of at least 0.5 cm$^3$/g.

5. The process as claimed in claim 1, wherein the alumina catalyst used is an alumina-metal oxide support material coated with aluminum chloride.

6. The process as claimed in claim 1, wherein a temperature is 200° C. to 350° C.

7. The process as claimed in claim 1, wherein the metal oxide is magnesium oxide.

* * * * *